(12) United States Patent
Lemanski et al.

(10) Patent No.: US 10,525,409 B2
(45) Date of Patent: Jan. 7, 2020

(54) PROCESSES AND SYSTEMS FOR REMOVING A VINYL IODIDE IMPURITY FROM A RECYCLE GAS STREAM IN THE PRODUCTION OF ETHYLENE OXIDE

(71) Applicant: SHELL OIL COMPANY, Houston, TX (US)

(72) Inventors: Michael Francis Lemanski, Houston, TX (US); Wayne Errol Evans, Richmond, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/061,794

(22) PCT Filed: Dec. 13, 2016

(86) PCT No.: PCT/EP2016/080752
§ 371 (c)(1),
(2) Date: Jun. 13, 2018

(87) PCT Pub. No.: WO2017/102701
PCT Pub. Date: Jun. 22, 2017

(65) Prior Publication Data
US 2018/0369752 A1  Dec. 27, 2018

(30) Foreign Application Priority Data

Dec. 15, 2015 (EP) .................................. 15200272

(51) Int. Cl.
*B01D 53/70* (2006.01)
*B01J 8/04* (2006.01)
(Continued)

(52) U.S. Cl.
CPC ............. *B01D 53/70* (2013.01); *B01D 53/02* (2013.01); *B01J 8/0492* (2013.01);
(Continued)

(58) Field of Classification Search
CPC ........ B01J 8/0419; B01J 8/0457; B01J 8/092; C07D 301/32
See application file for complete search history.

(56) References Cited

U.S. PATENT DOCUMENTS 2,289,063 A  7/1942  Ocon et al.
4,048,096 A  9/1977  Bissot
(Continued)

FOREIGN PATENT DOCUMENTS

DE  202012012866 U1  2/2014
EP  0776890 A2  6/1997
(Continued)

OTHER PUBLICATIONS

International Search Report and Written Opinion received for PCT Patent Application No. PCT/EP2016/080744, dated Mar. 14, 2017, 12 pages.
(Continued)

*Primary Examiner* — Lessanework Seifu
(74) *Attorney, Agent, or Firm* — James D. Carruth (57) ABSTRACT

Processes for reducing the amount of a gaseous iodide-containing impurity present in a recycle gas stream used in the production of ethylene oxide, in particular a vinyl iodide impurity, are provided. Processes for producing ethylene oxide, ethylene carbonate and/or ethylene glycol, and associated reaction systems are similarly provided.

15 Claims, 4 Drawing Sheets

(51) Int. Cl.
  *B01D 53/02* (2006.01)
  *C07D 301/10* (2006.01)
  *C07D 301/32* (2006.01)
  *C07C 21/17* (2006.01)
  *C07C 31/20* (2006.01)

(52) U.S. Cl.
  CPC ......... *C07D 301/10* (2013.01); *C07D 301/32* (2013.01); *B01D 2253/106* (2013.01); *B01D 2253/25* (2013.01); *B01D 2257/2068* (2013.01); *B01D 2257/504* (2013.01); *C07C 21/17* (2013.01); *C07C 31/202* (2013.01)

(56) References Cited

U.S. PATENT DOCUMENTS

| | | |
|---|---|---|
| 4,761,394 A | 8/1988 | Lauritzen |
| 4,766,105 A | 8/1988 | Lauritzen |
| 4,789,528 A | 12/1988 | Owen et al. |
| 5,179,057 A | 1/1993 | Bartley |
| 5,189,004 A | 2/1993 | Bartley |
| 5,380,697 A | 1/1995 | Matusz et al. |
| 5,739,075 A | 4/1998 | Matusz |
| 6,040,467 A | 3/2000 | Papavassiliou et al. |
| 6,368,998 B1 | 4/2002 | Lockemeyer |
| 6,656,874 B2 | 12/2003 | Lockemeyer |
| 7,030,056 B2 | 4/2006 | Birke et al. |
| 7,193,094 B2 | 3/2007 | Chipman et al. |
| 7,425,647 B2 | 9/2008 | Lemanski et al. |
| 8,193,374 B2 * | 6/2012 | Evans .................. B01D 53/02 549/230 |
| 8,546,592 B2 | 10/2013 | Evans et al. |
| 8,921,586 B2 | 12/2014 | Matusz |
| 8,932,979 B2 | 1/2015 | Matusz et al. |
| 2003/0204101 A1 * | 10/2003 | Jewson .................. B01J 29/89 549/533 |
| 2006/0070918 A1 | 4/2006 | Seapan et al. |
| 2008/0281118 A1 | 11/2008 | Matusz |
| 2011/0034710 A1 | 2/2011 | Matusz |
| 2017/0291119 A1 | 10/2017 | Wilkinson et al. |

FOREIGN PATENT DOCUMENTS

| | | |
|---|---|---|
| EP | 2279182 A1 | 2/2011 |
| GB | 2107712 A | 5/1983 |
| WO | 9908790 A1 | 2/1999 |
| WO | 9908791 A1 | 2/1999 |
| WO | 2008144402 A2 | 11/2008 |
| WO | 2009021830 A1 | 2/2009 |
| WO | 2009140319 A1 | 11/2009 |
| WO | 2016001348 A1 | 1/2016 |
| WO | 2017102694 A1 | 6/2017 |
| WO | 2017102698 A1 | 6/2017 |

OTHER PUBLICATIONS

International Search Report and Written Opinion received for PCT Patent Application No. PCT/EP2016/080749, dated Feb. 17, 2017, 8 pages.
International Search Report and Written Opinion received for PCT Patent Application No. PCT/EP2016/080752, dated Apr. 4, 2017, 9 pages.
International Search Report and Written Opinion received for PCT Patent Application No. PCT/EP2016/080759, dated Apr. 4, 2017, 9 pages.
Evans et al., "Industrial Epoxidation Processes", Industrial Epoxidation Processes, Encyclopedia of Catalysis (Wiley-Interscience), 2003, vol. 3, p. 246-264.
Brunauer et al., "Adsorption of Gases in MultiMolecular Layers", Journal of American Chemical Society, Feb. 1938, vol. 60, Issue No. 2, pp. 309-319.
Kirk-Othmer, Encyclopedia of Chemical Technology, 4th Edition, vol. 9, pp. 915-959.

* cited by examiner

PROCESSES AND SYSTEMS FOR REMOVING A VINYL IODIDE IMPURITY FROM A RECYCLE GAS STREAM IN THE PRODUCTION OF ETHYLENE OXIDE

CROSS REFERENCE TO RELATED APPLICATION

This is a national stage application of International application No. PCT/EP2016/080752, filed 13 Dec. 2016, which claims benefit of priority of European application No. 15200272.1, filed 15 Dec. 2015.

FIELD OF THE INVENTION

The present invention relates to a process and reaction system for the preparation of ethylene oxide, ethylene carbonate and/or ethylene glycol from ethylene.

BACKGROUND

Monoethylene glycol is used as a raw material in the manufacture of polyester fibres, polyethylene terephthalate (PET) plastics and resins. It is also incorporated into automobile antifreeze liquids. Ethylene carbonate is typically used as a solvent.

Monoethylene glycol can be commercially prepared from ethylene oxide by various known methods. These methods, although varied, all generally involve a two-stage reaction system, wherein ethylene is first converted to ethylene oxide, which is then converted to ethylene glycol. In most industrial-scale glycol production operations, the process for the production and recovery of ethylene oxide is integrated with the process for the production of ethylene glycol to maximize energy utilization and reduce costs.

In the first stage, ethylene oxide is typically produced by reacting ethylene with air or elemental oxygen in the presence of a suitable catalyst, such as a silver-based epoxidation catalyst, and often in the presence of organic moderators, such as organic halides, in an epoxidation reactor. (see Kirk Othmer's Encyclopedia of Chemical Technology, $4^{th}$ edition, Vol. 9, pages 923-940). This reaction generally occurs at pressures of 10-30 bar and temperatures of 200-300° C., and produces an epoxidation reaction product comprising ethylene oxide, unreacted reactants (such as ethylene and oxygen), various impurities (such as aldehyde impurities, including formaldehyde and acetaldehyde) and optionally other gases and/or by-products (such as nitrogen, argon, methane, ethane, water and/or carbon dioxide).

In the second stage, ethylene oxide is converted to ethylene glycol by one of several methods. In one well known method, the epoxidation reaction product from the epoxidation reactor is supplied to an ethylene oxide absorber, along with a recirculating absorbent solution, typically referred to as "lean absorbent", to absorb the ethylene oxide from the epoxidation reaction product. The ethylene oxide absorber produces an aqueous product stream comprising ethylene oxide, commonly referred to as "fat absorbent", which is then supplied to an ethylene oxide stripper, wherein steam is usually introduced counter-currently to separate the ethylene oxide as a vapor stream. The separated ethylene oxide is withdrawn at or near the top of the ethylene oxide stripper, as a more concentrated aqueous ethylene oxide stream, while an aqueous stream withdrawn from the ethylene oxide stripper as bottoms is typically recirculated to the ethylene oxide absorber for reuse as lean absorbent. The aqueous ethylene oxide stream withdrawn from the ethylene oxide stripper is then further reacted to provide ethylene glycol, either by direct hydrolysis in a hydrolysis reactor (i.e., by thermally reacting ethylene oxide with a large excess of water) or alternatively, by reacting the ethylene oxide with carbon dioxide in a carboxylation reactor in the presence of a carboxylation catalyst to produce ethylene carbonate. The ethylene carbonate may then be supplied, along with water, to a hydrolysis reactor and subjected to hydrolysis in the presence of a hydrolysis catalyst to provide ethylene glycol. Direct hydrolysis of ethylene oxide typically produces a glycol product of approximately 90-92 wt. % monoethylene glycol (MEG) (with the remainder being predominately diethylene glycol (DEG), some triethylene glycol (TEG), and a small amount of higher homologues), whereas the reaction via the ethylene carbonate intermediary typically produces a glycol product in excess of 99 wt. % MEG.

Efforts have been made to simplify the process for obtaining ethylene glycol from ethylene oxide, reducing the equipment that is required and reducing the energy consumption. For example, GB 2107712 describes a process for preparing monoethylene glycol wherein the gases from the epoxidation reactor are supplied directly to a reactor wherein ethylene oxide is converted to ethylene carbonate or to a mixture of ethylene glycol and ethylene carbonate.

Similarly, EP 0776890 describes a process wherein the gases from the epoxidation reactor are supplied to an ethylene oxide absorber, wherein the absorbing solution mainly contains ethylene carbonate and ethylene glycol. The ethylene oxide in the absorbing solution is supplied to a carboxylation reactor and allowed to react with carbon dioxide in the presence of a carboxylation catalyst, such as an iodide-containing carboxylation catalyst. The ethylene carbonate in the absorbing solution is subsequently supplied, with the addition of water, to a hydrolysis reactor and subjected to hydrolysis in the presence of a hydrolysis catalyst, such as an alkali metal hydroxide.

EP 2178815 describes a reactive absorption process for preparing monoethylene glycol, wherein the gases from the epoxidation reactor are supplied to an absorber and the ethylene oxide is contacted with lean absorbent comprising at least 20 wt. % water in the presence of one or more catalysts that promote carboxylation and hydrolysis and the majority of the ethylene oxide is converted to ethylene carbonate or ethylene glycol in the absorber.

In each of these cases, a recycle gas stream containing gases that are not absorbed by the recirculating absorbent stream will be produced from the ethylene oxide absorber. Typically, at least a portion of this recycle gas stream is treated in a carbon dioxide absorption column and then recombined with any portion of the recycle gas stream bypassing the carbon dioxide absorption column. The combined gases are then recycled to the epoxidation reactor.

However, it has been found that in those processes where the carboxylation reaction is performed in the ethylene oxide absorber using an iodide-containing carboxylation catalyst, decomposition materials and side products may be present in the recycle gas stream and/or in the fat absorbent stream. Examples of such decomposition materials and side products include gaseous iodide-containing impurities, such as alkyl iodides (e.g., methyl iodide, ethyl iodide, etc.) and vinyl iodide.

The silver-based epoxidation catalysts typically used in an epoxidation reactor are susceptible to catalyst poisoning, in particular, poisoning by gaseous iodide-containing impurities, such as alkyl iodides and vinyl iodide. Catalyst poisoning impacts the epoxidation catalyst performance, in particular the selectivity and/or the activity, and shortens the length of time the epoxidation catalyst can remain in the epoxidation reactor before it becomes necessary to exchange the catalyst with fresh catalyst. Accordingly, it is desirable to remove such catalyst poisons as much as is practicable from the recycle gas stream before it comes into contact with the epoxidation catalyst. For example, the use of a purification zone or a guard bed upstream of an epoxidation reactor is disclosed in EP 2285795, EP 2279182 and EP 2155375.

The present inventors have found that the sensitivity of epoxidation catalysts to certain gaseous iodide-containing impurities, particularly alkyl iodides and vinyl iodide, is even greater than previously expected. The present inventors have, therefore, sought to provide improved guard bed materials and improved processes to remove certain gaseous iodide-containing impurities from a recycle gas stream in the manufacture of ethylene oxide, ethylene carbonate and/or ethylene glycol.

SUMMARY

Accordingly, in one aspect, a process for producing ethylene oxide is provided, the process comprising:

contacting at least a portion of a recycle gas stream comprising a vinyl iodide impurity with a guard bed material to yield a treated recycle gas stream, wherein the guard bed material comprises a support material, palladium and gold; and contacting an epoxidation feed gas comprising ethylene, oxygen and at least a portion of the treated recycle gas stream with an epoxidation catalyst to yield an epoxidation reaction product comprising ethylene oxide.

Further, in accordance with another aspect, a process for producing ethylene carbonate and/or ethylene glycol is provided, the process comprising:

contacting at least a portion of a recycle gas stream comprising a vinyl iodide impurity with a guard bed material to yield a treated recycle gas stream, wherein the guard bed material comprises a support material, palladium and gold;

contacting an epoxidation feed gas comprising ethylene, oxygen and at least a portion of the treated recycle gas stream with an epoxidation catalyst to yield an epoxidation reaction product comprising ethylene oxide; and contacting at least a portion of the epoxidation reaction product comprising ethylene oxide with lean absorbent in the presence of an iodide-containing carboxylation catalyst to yield a fat absorbent stream comprising ethylene carbonate and/or ethylene glycol and the recycle gas stream comprising the vinyl iodide impurity.

Further, in accordance with yet another aspect, a reaction system for the production of ethylene carbonate and/or ethylene glycol is provided, the reaction system comprising:

a recycle gas loop fluidly connected to a source of ethylene and oxygen;

an epoxidation reactor comprising an epoxidation catalyst, an inlet, and an outlet, wherein the inlet of the epoxidation reactor is fluidly connected to the recycle gas loop;

an ethylene oxide absorber comprising an iodide-containing carboxylation catalyst, an inlet, and an outlet, wherein the outlet of the epoxidation reactor is fluidly connected to the inlet of the ethylene oxide absorber, the outlet of the ethylene oxide absorber is fluidly connected to the recycle gas loop, and the ethylene oxide absorber is configured to produce a recycle gas stream comprising a vinyl iodide impurity and a fat absorbent stream comprising ethylene carbonate and/or ethylene glycol; and a guard bed system comprising an inlet, an outlet, and one or more guard bed vessels comprising a guard bed material, wherein the guard bed material comprises a support material, palladium and gold, wherein the inlet and the outlet of the guard bed system is fluidly connected to the recycle gas loop, and the guard bed material is configured to remove at least a portion of the vinyl iodide impurity from at least a portion of the recycle gas stream.

BRIEF DESCRIPTION OF THE DRAWINGS

Some specific example embodiments of the disclosure may be understood by referring, in part, to the following description and the accompanying drawings.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DETAILED DESCRIPTION

It has been found that when ethylene oxide is catalytically reacted in the ethylene oxide absorber in the presence of an iodide-containing carboxylation catalyst, then gaseous iodide-containing impurities may be formed which exit the ethylene oxide absorber with the recycle gas stream. These gaseous iodide-containing impurities, particularly alkyl iodides and vinyl iodide, can poison the epoxidation catalyst in the epoxidation reactor, even in minute quantities.

Treating the recycle gas stream by contacting the stream with a guard bed material capable of at least partially absorbing such iodide-containing impurities can reduce the amount of such impurities in the recycle gas stream and thus protect the performance of the epoxidation catalyst, in particular the selectivity and/or activity of the catalyst, as well as the duration of time the epoxidation catalyst can remain in the epoxidation reactor before it becomes necessary to exchange the catalyst with fresh epoxidation catalyst.

Accordingly, described herein are processes and associated systems for producing ethylene oxide, ethylene carbonate and/or ethylene glycol wherein a recycle gas stream comprising a vinyl iodide impurity is contacted with a guard bed material that comprises a support material, palladium and gold to reduce the amount of the vinyl iodide impurity present in the recycle gas stream.

By using the processes and systems disclosed herein, the amount of a vinyl iodide impurity present in a recycle gas stream is reduced to the very low levels the present inventors have now found to be required for the performance of the epoxidation catalyst to remain substantially unaffected by its presence. In particular, the amount of vinyl iodide present in a treated recycle gas stream is preferably no more than 20 ppbv, preferably no more than 15 ppbv, preferably no more than 10 ppbv, preferably no more than 5 ppbv, more preferably no more than 4 ppbv, even more preferably no more than 3 ppbv, most preferably no more than 1 ppbv. Similarly, the amount of vinyl iodide present in the epoxidation feed gas supplied to the epoxidation reactor is preferably no more than 20 ppbv, preferably no more than 15 ppbv, preferably no more than 10 ppbv, preferably no more than 5 ppbv, more preferably no more than 4 ppbv, even more preferably no more than 3 ppbv, most preferably no more than 1 ppbv.

Figure 1:
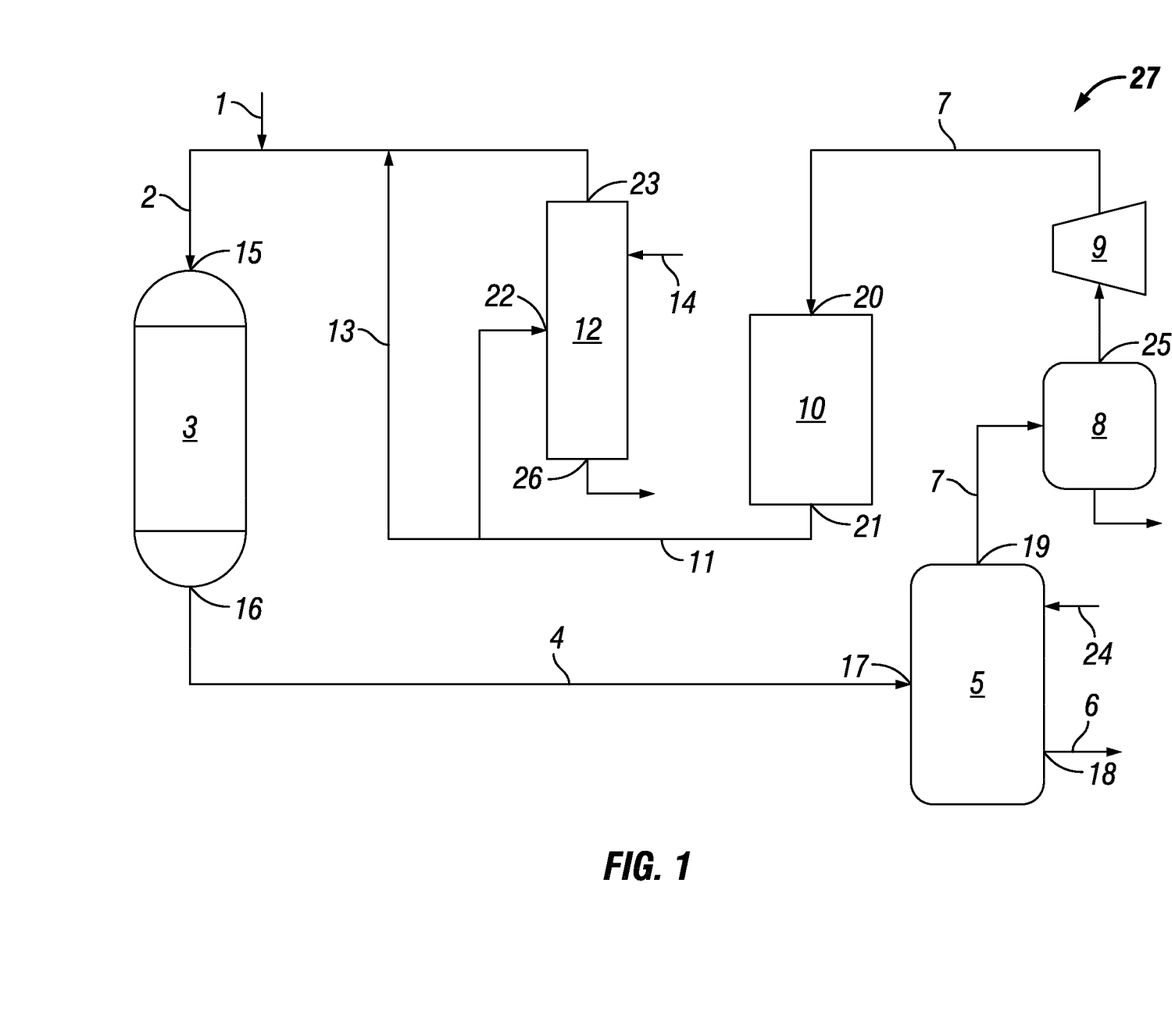
FIGS. 1-4 are schematic illustrations showing exemplary embodiments of the present disclosure.

Reference is made to FIG. 1, which is a schematic view of a reaction system (27) for the production of ethylene carbonate and/or ethylene glycol, according to an embodiment of the present disclosure. Reaction system (27) generally comprises epoxidation reactor (3), ethylene oxide absorber (5), guard bed system (10) and carbon dioxide absorber (12). It will be clear to the skilled person, that as schematic diagrams these figures do not show all necessary inputs, outputs, recycle streams, etc. that may be present in the reaction system. Furthermore, in the figures herein, as will be appreciated, elements can be added, exchanged, and/or eliminated so as to provide any number of additional embodiments and the sequence in which various feed components are introduced into the process and their respective points of introduction, as well as the flow connections, may be varied from that depicted. In addition, as will be appreciated, the proportion and the relative scale of the elements provided in the figure are intended to illustrate the embodiments of the present disclosure, and should not be taken in a limiting sense.

As shown in FIG. 1, epoxidation feed gas (2) is supplied to epoxidation reactor (3) via an inlet, such as inlet (15), which is in fluid communication with the recycle gas loop. Components of epoxidation feed gas (2) include at least a portion of treated recycle gas stream (11) and typically further comprise ethylene, oxygen, ballast gas (e.g., methane or nitrogen), and a reaction modifier (e.g., monochloroethane, vinyl chloride or dichloroethane), which may be supplied to the recycle gas loop via one or more inlets, such as inlet (1).

In epoxidation reactor (3), ethylene is reacted with oxygen in the presence of an epoxidation catalyst to yield epoxidation reaction product stream (4), which typically comprises ethylene oxide, unreacted ethylene and oxygen, reaction modifier, ballast gas, various by-products of the epoxidation reaction (e.g., carbon dioxide and water) and various impurities. Epoxidation reaction product stream (4) exits epoxidation reactor (3) via an outlet, such as outlet (16), which is in fluid communication with an inlet of ethylene oxide absorber (5), such as inlet (17). Preferably, epoxidation reaction product stream (4) is cooled in one or more coolers (not shown), preferably with generation of steam at one or more temperature levels before being supplied to ethylene oxide absorber (5).

Epoxidation reaction product stream (4) and lean absorbent stream (24) are supplied to ethylene oxide absorber (5). In ethylene oxide absorber (5), the epoxidation reaction product is brought into intimate contact with the lean absorbent in the presence of an iodide-containing carboxylation catalyst, and more preferably in the presence of an iodide-containing carboxylation catalyst and a hydrolysis catalyst. At least a portion of, and preferably substantially all of, the ethylene oxide in the epoxidation reaction product is absorbed into the lean absorbent. Fat absorbent stream (6), which comprises ethylene carbonate and/or ethylene glycol, is withdrawn from ethylene oxide absorber (5) via an outlet, such as outlet (18) and may optionally be supplied to one or more finishing reactors (not shown).

Any gases not absorbed in ethylene oxide absorber (5) are withdrawn at or near the top of ethylene oxide absorber (5) as recycle gas stream (7) via an outlet, such as outlet (19), which is in fluid communication with the recycle gas loop. The recycle gas loop comprises interconnecting pipework between outlet (19) of ethylene oxide absorber (5) and inlet (15) of epoxidation reactor (3) and optionally may further comprise heat exchanger(s), a vapor-liquid separator, such as vapor-liquid separator (8) (e.g., knock-out vessel, flash vessel, etc.), a recycle gas compressor, such as recycle gas compressor (9), and/or a carbon dioxide absorber, such as carbon dioxide absorber (12).

Recycle gas stream (7) comprises a vinyl iodide impurity due to the presence of the iodide-containing carboxylation catalyst in ethylene oxide absorber (5) and the reaction conditions therein. Optionally, the recycle gas stream may further comprise an alkyl iodide impurity, such as methyl iodide, ethyl iodide, or a combination thereof. Typically, recycle gas stream (7) further comprises one or more of ethylene, oxygen, reaction modifier, ballast gas, carbon dioxide and water. To reduce the amount of the vinyl iodide impurity, recycle gas stream (7) is supplied to guard bed system (10) via an inlet, such as inlet (20) that is in fluid communication with the recycle gas loop.

In guard bed system (10), recycle gas stream (7) is brought into contact with a packed bed of guard bed material in a guard bed vessel. The guard bed material comprises a support material, palladium and gold. By contacting recycle gas stream (7) with the guard bed material, at least a portion of the vinyl iodide impurity is removed from recycle gas stream (7) to yield treated recycle gas stream (11), which comprises a reduced amount of the vinyl iodide impurity relative to recycle gas stream (7). Treated recycle gas stream (11) exits guard bed system (10) via an outlet, such as outlet (21), which is in fluid communication with the recycle gas loop.

Figure 3:
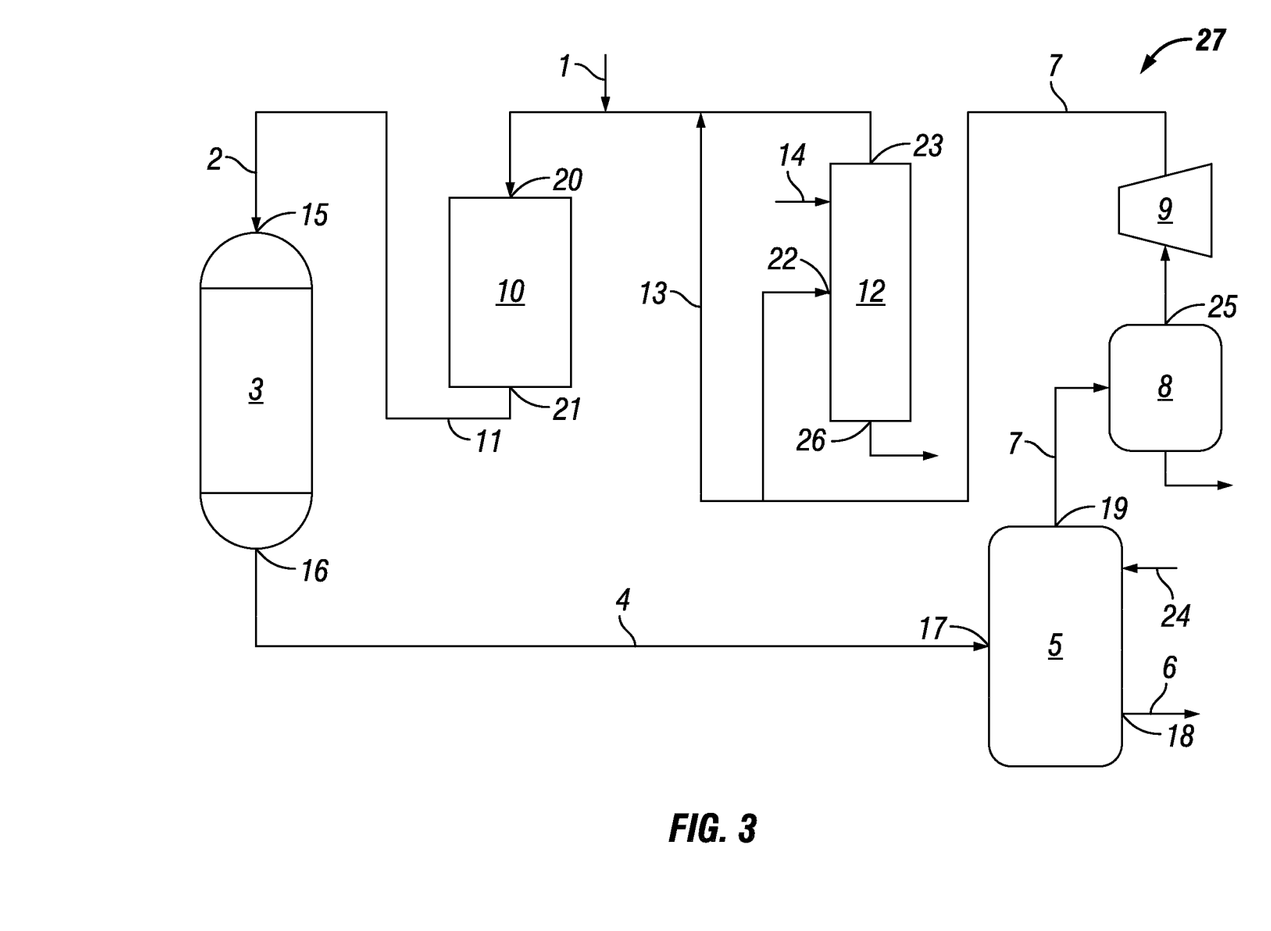

Suitably, guard bed system (10) may be located anywhere in the recycle gas loop. For example, as shown in FIG. 1, guard bed system (10) may preferably be located in the recycle gas loop between outlet (19) of ethylene oxide absorber (5) and an inlet of carbon dioxide absorber (12), such as inlet (22), and more preferably between an outlet of recycle gas compressor (9) and inlet (22) of carbon dioxide absorber (12). Also, as shown in FIG. 1, guard bed system (10) may preferably be located in the recycle gas loop between an outlet of vapor-liquid separator (8), such as outlet (25), and inlet (15) of epoxidation reactor (3), and more preferably between outlet (25) of vapor-liquid separator (8) and inlet (22) of carbon dioxide absorber (12). Further, as shown in FIG. 1, guard bed system (10) may preferably be located in the recycle gas loop upstream from inlet (1), where additional component(s) of epoxidation feed gas (2), such as ethylene, oxygen, ballast gas and/or a reaction modifier, may be supplied to the recycle gas loop, or alternatively, downstream from such a point, as shown in FIG. 3, for example.

Preferably, as shown in FIG. 1, at least a portion of treated recycle gas stream (11) is supplied to carbon dioxide absorber (12) via an inlet, such as inlet (22), along with recirculating absorbent stream (14). In carbon dioxide absorber (12), the treated recycle gas stream is brought into contact with recirculating absorbent stream (14). At least a portion of the carbon dioxide in the treated recycle gas stream is absorbed into the recirculating absorbent stream and is withdrawn from carbon dioxide absorber (12) via an outlet, such as outlet (26). The portion of the treated recycle gas stream that was supplied to carbon dioxide absorber (12), but that was not absorbed by the recirculating absorbent stream exits via an outlet, such as outlet (23), and is preferably re-combined with any portion of the treated recycle gas stream that bypassed carbon dioxide absorber (12) via bypass (13). The treated recycle gas stream is then recycled to inlet (15) of epoxidation reactor (3) as a component of epoxidation feed gas (2).

Optionally, one or more heating or cooling devices, such as a heat exchanger, may be present in the recycle gas loop in order to alter the temperature of recycle gas stream (7) (e.g., so as to provide recycle gas stream (7) to guard bed system (10) at an optimal temperature) and/or in order to alter the temperature of treated recycle gas stream (11) (e.g., so as to provide treated recycle gas stream (11) to epoxidation reactor (3)) or for any further treatment of the treated recycle gas stream prior to being provided to epoxidation reactor (3).

Figure 2:
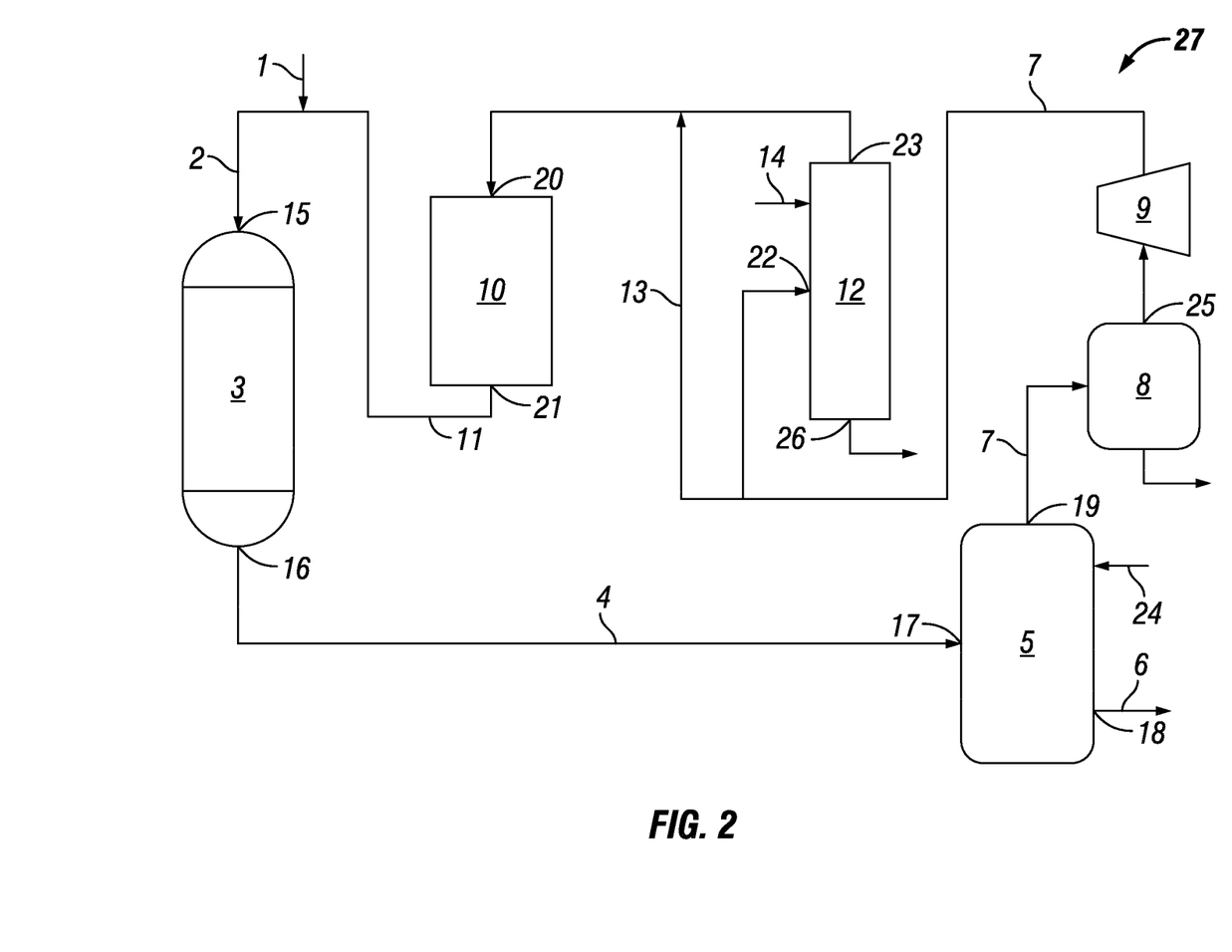

FIG. 2 is a schematic view of a reaction system (27) for the production of ethylene carbonate and/or ethylene glycol, similar to FIG. 1 except that guard bed system (10) is positioned in the recycle gas loop downstream from carbon dioxide absorber (12). As shown in FIG. 2, at least a portion of recycle gas stream (7) is supplied to inlet (22) of carbon dioxide absorber (12), while the remaining portion of recycle gas stream (7) (if any) bypasses carbon dioxide absorber (12) via bypass (13). The portion of the recycle gas stream that was supplied to carbon dioxide absorber (12), but that was not absorbed by the recirculating absorbent stream exits via outlet (23), and is preferably re-combined with any portion of the recycle gas stream that bypassed carbon dioxide absorber (12) via bypass (13) and is supplied to inlet (20) of guard bed system (10). Treated recycle gas stream (11) exits guard bed system (10) via outlet (21), which is in fluid communication with the recycle gas loop, and is recycled to inlet (15) of epoxidation reactor (3) as a component of epoxidation feed gas (2).

FIG. 3 is a schematic view of a reaction system (27) for the production of ethylene carbonate and/or ethylene glycol, similar to FIG. 2 except that guard bed system (10) is positioned in the recycle gas loop downstream from inlet (1), where one or more additional components of epoxidation feed gas (2), such as ethylene, oxygen, ballast gas and/or a reaction modifier, may be supplied to the recycle gas loop.

Figure 4:
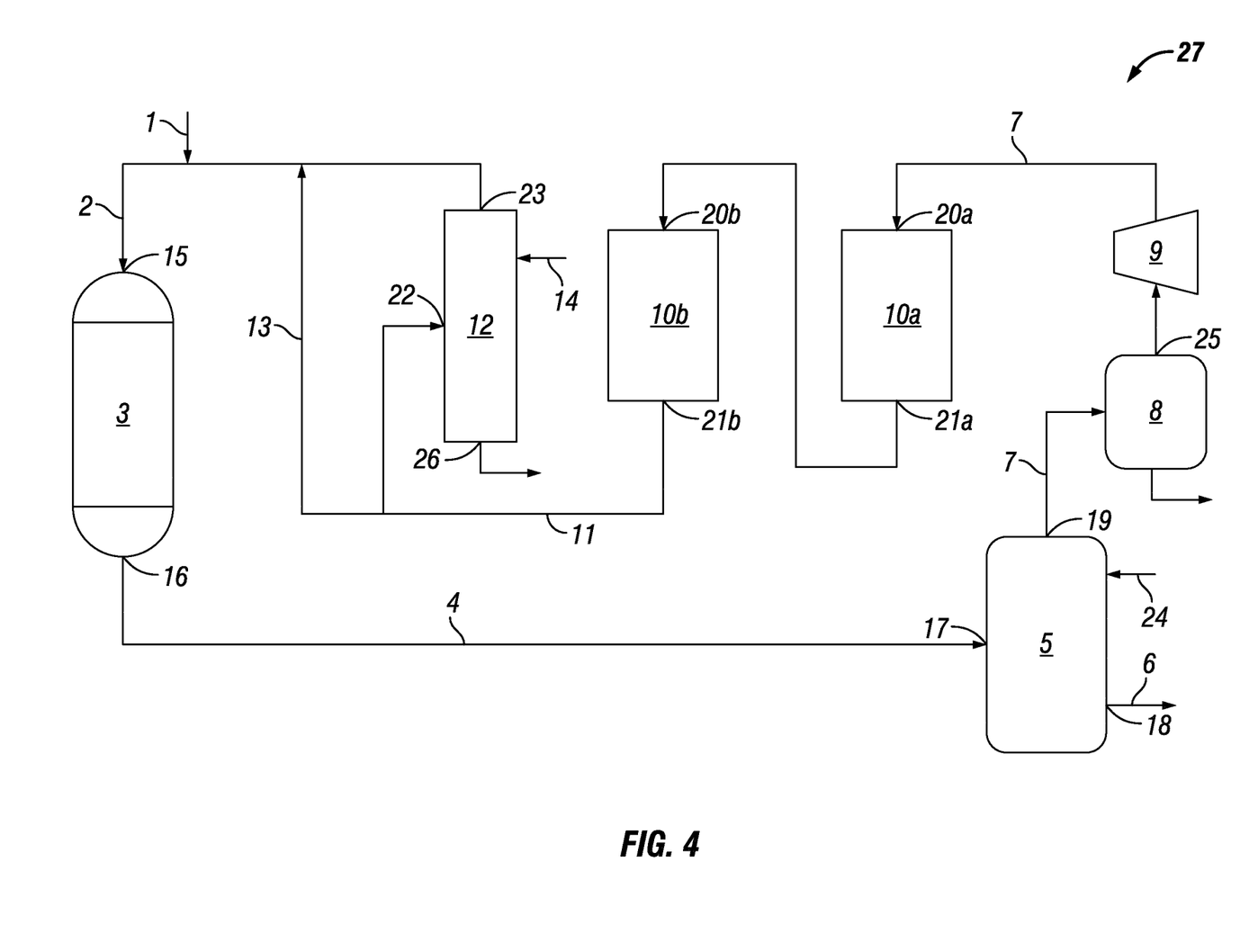

FIG. 4 is a schematic view of a reaction system (27) for the production of ethylene carbonate and/or ethylene glycol, similar to FIG. 1 except that the guard bed system comprises a plurality of guard bed vessels. As shown in FIG. 4, recycle gas stream (7) is supplied via inlet (20a) to a guard bed system comprising two guard bed vessels (10a) and (10b) that each comprise a packed bed of guard bed material. The gas stream exiting guard bed vessel (10a) via outlet (21a) is subsequently supplied to guard bed vessel (10b) via inlet (20b). Treated recycle gas stream (11) exits the guard bed system via outlet (21b), which is in fluid communication with the recycle gas loop. Preferably, at least a portion of treated recycle gas stream (11) is supplied to carbon dioxide absorber (12) before it is recycled to inlet (15) of epoxidation reactor (3) as a component of epoxidation feed gas (2).

A guard bed system of the present disclosure comprises an inlet, an outlet and one or more guard bed vessels comprising a guard bed material. Suitably, the inlet of the guard bed system is fluidly connected to the recycle gas loop so that at least a portion of a recycle gas stream from the ethylene oxide absorber is supplied (either directly or indirectly) to the guard bed system. Within the guard bed system, the recycle gas stream passes through the one or more guard bed vessels and contacts a guard bed material whereby vinyl iodide impurities are removed. A treated recycle gas stream is removed from an outlet of the guard bed system. Said treated recycle gas stream will contain a reduced amount of vinyl iodide as compared to the recycle gas stream. Suitably, the outlet of the guard bed system is fluidly connected to the recycle gas loop so that at least a portion of a treated recycle gas stream from the guard bed system is supplied (either directly or indirectly) to an inlet of the epoxidation reactor.

Preferably, a guard bed system comprises two or more guard bed vessels. Optionally, the guard bed system comprises more than two, for example three or four, guard bed vessels. When two or more guard bed vessels are present in the guard bed system, the guard bed vessels may be arranged in parallel with associated switching means to allow the process to be switched between the vessels, thus maintaining a continuous operation of the process. Alternatively, the guard bed vessels within the guard bed system may be arranged in series or in series in sequential order, with associated valves, as described in co-pending application EP 15200254.9, which is incorporated by reference herein.

A guard bed vessel suitable for use in the present disclosure includes any vessel in which a bed of guard bed material can be held and through which a recycle gas stream can be passed such that the recycle gas stream comes into contact with the guard bed material. Preferably, the guard bed vessel is a fixed bed reactor, such as an axial fixed bed reactor, wherein the recycle gas stream is contacted with the guard bed material as an axial flow; or a radial flow fixed bed reactor, wherein the recycle gas stream is supplied from an inlet to the outside of the fixed bed and passes through the fixed bed to the center of the guard bed vessel and then to an outlet. A radial flow fixed bed reactor is particularly preferred because it will generally produce less of a pressure drop across the bed of guard bed material. Other suitable types of guard bed vessels will be apparent to those of ordinary skill in the art and are to be considered within the scope of the present disclosure.

Without wishing to be bound by any particular theory, it is believed that by contacting a recycle gas stream comprising a vinyl iodide impurity with a guard bed material of the present disclosure, at least a portion of the vinyl iodide impurity present in the recycle gas stream is removed by chemical or physical means including, but not limited to, reaction with the impurity and absorption of the impurity.

The operating conditions within the one or more guard bed vessels in the guard bed system can be adjusted according to overall processing conditions. In general, the pressure in the one or more guard bed vessels in the guard bed system is determined by the pressure of the recycle gas loop. Preferably, the operating pressure can range from 1 to 4 MPa (gauge), more preferably from 2 to 3 MPa (gauge). Additionally, a guard bed vessel in the guard bed system is generally operated at an elevated temperature (relative to ambient).

Preferably, the one or more guard bed vessels in the guard bed system are operated at a temperature of at least 65° C., more preferably at least 70° C., most preferably at least 83° C. Further, the one or more guard bed vessels in the guard bed system are preferably operated at a temperature of at most 95° C., more preferably at most 90° C., most preferably at most 87° C., or from 65° C. to 95° C., or from 70° C. to 90° C., or from 83° C. to 87° C.

Optionally, a guard bed system may be preceded or followed by a further guard bed device. Such a guard bed device may be of a standard set up known in the art, such as a simple, single bed, guard bed vessel or two such guard beds arranged in parallel or in series to allow the feed to be switched between the two.

The one or more guard bed vessels each comprise a bed of guard bed material. It is preferred that all guard bed vessels within the guard bed system contain the same guard bed material. Suitable bed dimensions of a bed of guard bed material may readily be determined using known engineering principles. Preferably, a guard bed vessel comprises a guard bed material present in a bed that is sized to provide a contact time of the guard bed material with the incoming recycle gas stream that is sufficient to provide the desired degree of removal of the vinyl iodide impurity from the recycle gas stream.

In accordance with the present disclosure, one or more guard bed vessels in a guard bed system comprise a guard bed material that comprises a support material, palladium (Pd) and gold (Au). With respect to suitable support materials, such support materials are generally known in the art. The specific support material used in the guard bed material is not particularly limited and therefore any of the conventional support materials heretofore used for the preparation of palladium-gold catalysts, which are typically used in the production of vinyl acetate by the vapor phase reaction of ethylene, acetic acid and oxygen, can be used. Illustrative of such support materials are those comprising silica, alumina, silica-alumina, silica gel, silicic acid, silicates, silicon carbide, titania, zirconia, tungsten trioxide, pumice, magnesia, zeolites, and combinations thereof. Preferably, the support material comprises silica, and may or may not further comprise alumina. In these embodiments, the silica content of the support material may be at least 50 wt. %, more typically at least 90 wt. %, based on the weight of the support material. Frequently, the silica content of the support material is at most 99.99 wt. %, more frequently at most 99.9 wt. %, on the same basis.

Suitable shapes for a support material include any of the wide variety of shapes known for such materials, which include, but are not limited to, particles, pills, chunks, tablets, pieces, pellets, rings, spheres, wagon wheels, trapezoidal bodies, doughnuts, amphora, rings, Raschig rings, honeycombs, monoliths, saddles, cylinders, hollow cylinders, multi-lobed cylinders, cross-partitioned hollow cylinders (e.g., cylinders having at least one partition extending between walls), cylinders having gas channels from side wall to side wall, cylinders having two or more gas channels, and ribbed or finned structures. While the cylinders are often circular, other cross-sections, such as oval, hexagonal, quadrilateral, trilateral, and multi-lobed may be useful. Additionally, the size of the support material is generally not limited, and may include any size suitable for use in a guard bed vessel. Preferably, the support material is in the form of particles or spheres having a diameter of from about 2 to 10 mm, or from 3 to 9 mm, or from 4 to 7 mm.

Suitable guard bed material further comprises palladium in an amount of at least 0.1% by weight and no more than 3% by weight, calculated as the amount of palladium relative to the total weight of the guard bed material. Preferably, the guard bed material comprises palladium in an amount of from 0.1% to 3% by weight, or from 0.5% to 2.5% by weight, or from 0.5% to 2.2% by weight, or from 0.8% to 2.2% by weight, or from 1% to 2% by weight, or at most 3% by weight, or at most 2.5% by weight, or at most 2.2% by weight, or at most 2% by weight, on the same basis. As used herein, unless otherwise specified, the total weight of the guard bed material is understood to refer to the weight of the support material and all components deposited thereon, including palladium and gold.

In addition to palladium, the guard bed material further comprises gold in an amount of at least 0.1% by weight and no more than 3% by weight, calculated as the amount of gold relative to the total weight of the guard bed material. Preferably, the guard bed material comprises gold in an amount of from 0.1% to 3% by weight, or from 0.1% to 2.5% by weight, or from 0.5% to 2% by weight, or from 0.5% to 1.5% by weight, or from 0.7% to 1.2% by weight, or from 0.5% to 1% by weight, or from 0.7% to 1% by weight, or at most 3% by weight, or at most 2.5% by weight, or at most 2% by weight, or at most 1.5% by weight, or at most 1% by weight, on the same basis. One example of a suitable guard bed material is KL7905, which is a spherical material comprising palladium and gold on a silica support commercially available from CRI Catalyst.

The specific manner in which a guard bed material is prepared is not limited, and therefore any known preparative method may be used, provided that the palladium and gold are provided on the support material in a suitable manner. In general, a guard bed material may be prepared by impregnating a support material with one or more aqueous impregnation solutions comprising palladium and gold. Further, an impregnated support material may optionally be contacted with a precipitating agent to precipitate palladium and/or gold from such impregnating solution(s) and/or contacted with a reducing agent to convert the palladium and/or gold into metallic species. As used herein, the phrase "impregnating a support material with one or more aqueous impregnation solutions comprising palladium and gold" and similar or cognate terminology means that the support material is impregnated in a single or multiple step with one aqueous impregnation solution comprising palladium and gold; or in multiple steps with two or more aqueous impregnation solutions, wherein each aqueous impregnation solution comprises at least one component selected from palladium and gold, with the proviso that palladium and gold will individually be found in at least one of the aqueous impregnation solutions. Furthermore, as is known in the art, the sequence of contacting the support material with one or more aqueous impregnation solutions comprising palladium and gold may vary. Thus, impregnation of palladium and gold may be effected coincidentally or sequentially. In more detail, the applicable materials and methods may include those as disclosed in U.S. Pat. Nos. 4,048,096, 5,179,057, 5,189,004, 7,425,647, WO 1999008790 and WO 1999008791, which are incorporated herein by reference.

Optionally, a support material be washed and/or treated prior to or subsequent impregnation. Any method known in the art for washing and/or treating may be used in accordance with the present disclosure, provided that such method does not negatively affect the performance of the guard bed material. Reference is made to U.S. Pat. Nos. 7,030,056 and 7,425,647 which are incorporated herein by reference.

Although guard bed materials suitable for use herein are typically prepared by impregnating a support material with one or more aqueous solutions (commonly referred to as "aqueous impregnation solution(s)") comprising palladium and gold, the present disclosure is not intended to be limited to any particular preparation method. Accordingly, any known preparative method may be used provided that palladium, gold, and any other optional components (if any) are provided on the support material in a suitable manner.

Following impregnation of the support material with the one or more aqueous impregnation solutions, the support material optionally may be contacted with a precipitating agent. A suitable precipitating agent may include, for example, alkali metal silicates, alkali metal hydroxides, alkali metal bicarbonates, alkali metal carbonates and combinations thereof. Suitable alkali metals are lithium, sodium, potassium and combinations thereof. Preferably, the precipitating agent is sodium silicate, such as sodium metasilicate and hydrated sodium metasilicate. Suitable precipitating agents and precipitation methods are known from U.S. Pat. Nos. 4,048,096, 5,179,057, 5,189,004, 7,030,056, and 742, 647, which are incorporated herein by reference.

Optionally, following impregnation of the support material with the one or more aqueous impregnation solutions or after precipitation, the support may be contacted with a reducing agent. A suitable reducing agent may include, for example, diborane; amines, such as ammonia and hydrazine; carboxylic acids and their salts, such as oxalic acid, potassium oxalate, formic acid, potassium formate, ammonium citrate; aldehydes, such as formaldehyde, acetaldehyde; hydrogen peroxide; reducing sugars such as glucose; alcohols other than reducing sugars, such as methanol and ethanol; polyhydric phenols, such as hydroquinone and catechol; hydrogen; carbon monoxide; olefins, such as ethylene, propene and isobutene; sodium borohydride; and combinations thereof. Suitable reducing agents and reduction methods are known from U.S. Pat. Nos. 4,048,096, 5,179,057, 5,189,004, 7,030,056, and 7,425,647, which are incorporated herein by reference.

In another embodiment, palladium and gold are precipitated and reduced to metallic species in one step, following, for example, procedures as disclosed in WO 1999008790 and WO 1999008791, which are herein incorporated by reference.

Optionally, guard bed materials suitable for use herein may further comprise an alkali metal. Typically, such a guard bed material may be prepared by impregnating a support material (or the guard bed material comprising palladium and gold) with a source of an alkali metal, such as those disclosed in U.S. Pat. Nos. 4,048,096, 5,179,057 and 5,189,004, which are herein incorporated by reference. Suitable sources of an alkali metal include, for example, alkali metal carbonates and alkali metal carboxylates. The alkali metal carboxylate is typically derived from a mono carboxylic acid, such as butyric acid, propionic acid and, preferably, acetic acid. The alkali metal may be any one or more of lithium, sodium, potassium, rubidium and cesium. Preferably, the alkali metal is potassium. The preferred alkali metal carboxylate is potassium acetate. The quantity of the alkali metal carboxylate is typically such that the alkali metal content of the guard bed material is in the range of from 0.1 to 5 mole/kg, more preferably from 0.2 to 2 mole/kg, for example 340 mmole/kg, or 585 mmole/kg, or 765 mmole/kg, or 1560 mmole/kg.

Optionally, at certain stages of the guard bed material preparation it may be desirable to perform a drying step. Drying is typically performed at a temperature in the range of from 50 to 300° C., more typically in the range of from 80 to 150° C., for example 90° C., or 115° C., or 120° C., using an inert gas, such as nitrogen or helium, or air.

Processes of the present disclosure further comprise contacting an epoxidation feed gas comprising ethylene, oxygen and at least a portion of the treated recycle gas stream with an epoxidation catalyst to yield an epoxidation reaction product comprising ethylene oxide. Although an epoxidation process may be carried out in a variety of known ways, it is preferred to carry out the epoxidation process as a continuous, gas-phase process, wherein an epoxidation feed gas is contacted with an epoxidation catalyst in the gas phase in an epoxidation reactor. The following description provides further details of the epoxidation catalyst, epoxidation reactor, epoxidation feed gas and the epoxidation process.

Suitable epoxidation catalysts that may be employed are known in the art and generally comprise a carrier, and deposited on the carrier, silver and optionally, one or more promoters, such a rhenium promoter, an alkali metal promoter, etc. Detailed preparative techniques for carriers and epoxidation catalysts are generally known in the art. For additional disclosure regarding suitable epoxidation catalysts and preparative techniques, reference may be made to, for example U.S. Pat. Nos. 4,761,394, 8,921,586 and 8,932,979 and U.S. Patent Publication Nos. 20080281118 and 20110034710, which are incorporated herein by reference.

An epoxidation reactor suitable for use in the systems and processes of the present disclosure may be any reactor vessel used to react ethylene and oxygen in the presence of an epoxidation catalyst, and comprises an inlet that is in fluid communication to the recycle gas loop and further comprises an outlet that is in fluid communication with an inlet of an ethylene oxide absorber. Suitable epoxidation reactors may include any of a wide variety of known reactor vessels, such as a fixed bed reactor (e.g., a fixed bed tubular reactor), a continuous stirred tank reactor (CSTR), a fluid bed reactor, etc. Additionally, a plurality of epoxidation reactors may be used in parallel. One commercial example of a suitable epoxidation reactor is a shell-and-tube heat exchanger comprising a plurality of reactor tubes, wherein the shell contains a coolant to regulate the temperature of the epoxidation reactor and wherein the plurality of tubes are parallel, elongated tubes that contain the epoxidation catalyst.

In accordance with the present disclosure, an epoxidation feed gas comprises ethylene, oxygen and a treated recycle gas stream. Optionally, the epoxidation feed gas may further comprise carbon dioxide, a ballast gas, a reaction modifier, and a combination thereof. As used herein, the term "epoxidation feed gas" refers to the totality of the gas stream supplied at the inlet of the epoxidation reactor, which may suitably be comprised of a combination of one or more gas stream(s), such as an ethylene stream, an oxygen stream, a treated recycle gas stream, etc. Further, it should be understood that the concentrations discussed below of individual feed components in the epoxidation feed gas reflect the total concentration of that component in the epoxidation feed gas, irrespective of the source(s).

Ethylene may be present in the epoxidation feed gas in a concentration that may vary over a wide range. However, ethylene is typically present in the epoxidation feed gas in a concentration of at least 5 mole-%, relative to the total epoxidation feed gas, or at least 8 mole-%, or at least 10 mole-%, or at least 12 mole-%, or at least 14 mole-%, or at least 20 mole-%, or at least 25 mole-%, on the same basis. Similarly, ethylene is typically present in the epoxidation feed gas in a concentration of at most 65 mole-%, or at most 60 mole-%, or at most 55 mole-%, or at most 50 mole-%, or at most 48 mole-%, on the same basis. In some embodiments, ethylene may be present in the epoxidation feed gas in a concentration of from 5 mole-% to 60 mole-%, relative to the total epoxidation feed gas, or from 10 mole-% to 50 mole-%, or from 12 mole-% to 48 mole-%, on the same basis.

In addition to ethylene, the epoxidation feed gas further comprises oxygen, which may be provided either as pure oxygen or air. See W. E. Evans, J. M. Kobe, M. F. Lemanski and R. L. June, "Industrial Epoxidation Processes", Encyclopedia of Catalysis (Wiley-Interscience), Volume 3, page 246 (2003). In an air-based process, air or air enriched with oxygen is employed, while in an oxygen-based process, high-purity (at least 95 mole-%) oxygen or very high purity (at least 99.5 mole-%) oxygen is employed. Reference may be made to U.S. Pat. No. 6,040,467, incorporated by reference herein, for further description of oxygen-based epoxidation processes. Presently, most epoxidation plants are oxygen-based, which is preferred. Typically, in oxygen-based processes, the epoxidation feed gas further comprises a ballast gas, which will be discussed in more detail below, to maintain the oxygen concentration below the maximum level allowed by flammability considerations.

In general, the oxygen concentration in the epoxidation feed gas should be less than the concentration of oxygen that would form a flammable mixture at either the inlet or the outlet of the epoxidation reactor at the prevailing operating conditions. Often, in practice, the oxygen concentration in the epoxidation feed gas may be no greater than a predefined percentage (e.g., 95%, 90%, etc.) of oxygen that would form a flammable mixture at either the inlet or the outlet of the epoxidation reactor at the prevailing operating conditions. Although the oxygen concentration may vary over a wide range, the oxygen concentration in the epoxidation feed gas is typically at least 0.5 mole-%, relative to the total epoxidation feed gas, or at least 1 mole-%, or at least 2 mole-%, or at least 3 mole-%, or at least 4 mole-%, or at least 5 mole-%, on the same basis. Similarly, the oxygen concentration of the epoxidation feed gas is typically at most 20 mole-%, relative to the total epoxidation feed gas, or at most 15 mole-%, or at most 12 mole-%, or at most 10 mole-%, on the same basis. In some embodiments, oxygen may be present in the epoxidation feed gas in a concentration of from 1 mole-% to 15 mole-%, relative to the total epoxidation feed gas, or from 2 mole-% to 12 mole-%, or from 3 mole-% to 10 mole-%, on the same basis. Typically, as the oxygen concentration in the epoxidation feed gas increases, the required operating temperature decreases. However as previously mentioned, in practice, flammability is generally the limiting factor for the maximum concentration of oxygen in the epoxidation feed gas. Accordingly, in order to remain outside the flammable regime, the oxygen concentration of the epoxidation feed gas may be lowered as the ethylene concentration of the epoxidation feed gas is increased. It is within the ability of one skilled in the art to determine a suitable concentration of oxygen to be included in the epoxidation feed gas, taking into consideration, for example, the overall epoxidation feed gas composition, along with the other operating conditions, such as pressure and temperature.

Optionally, the epoxidation feed gas may further comprise carbon dioxide. When present, carbon dioxide is typically present in the epoxidation feed gas in a concentration of 0.10 mole-% or greater, relative to the total epoxidation feed gas, or 0.12 mole-% or greater, or 0.15 mole-% or greater, or 0.17 mole-% or greater, or 0.20 mole-% or greater, or 0.22 mole-% or greater, or 0.25 mole-% or greater, on the same basis. Similarly, carbon dioxide is generally present in the epoxidation feed gas in a concentration of at most 10 mole-%, relative to the total epoxidation feed gas, or at most 8 mole-%, or at most 5 mole-%, or at most 3 mole-%, or at most 2.5 mole-%, on the same basis. In some embodiments, carbon dioxide may be present in the epoxidation feed gas in a concentration of from 0.10 mole-% to 10 mole-%, relative to the total epoxidation feed gas, or from 0.15 mole-% to 5 mole-%, or from 0.20 mole-% to 3 mole-%, or from 0.25 mole-% to 2.5 mole-%, on the same basis. Carbon dioxide is produced as a by-product of the epoxidation reaction and is typically introduced into the epoxidation feed gas as a component of the treated recycle gas stream. Carbon dioxide generally has an adverse effect on catalyst performance, with the operating temperature increasing as the concentration of carbon dioxide present in the epoxidation feed gas increases. Accordingly, in the commercial production of ethylene oxide, it is common for at least a portion of the carbon dioxide to be continuously removed (e.g., via a carbon dioxide absorber) to maintain the concentration of carbon dioxide in the epoxidation feed gas at an acceptable level.

The epoxidation feed gas optionally may further comprise a ballast gas, such as nitrogen, methane, or a combination thereof. When used, a ballast gas may be added to the epoxidation feed gas to increase the oxygen flammability concentration. If desired, a ballast gas may be present in the epoxidation feed gas in a concentration of at least 5 mole-%, relative to the total epoxidation feed gas, or at least 10 mole-%, or at least 20 mole-%, or at least 25 mole-%, or at least 30 mole-%, on the same basis. Similarly, a ballast gas may be present in the epoxidation feed gas in a concentration of at most 80 mole-%, relative to the total epoxidation feed gas, or at most 75 mole-%, or at most 70 mole-%, or at most 65 mole-%, on the same basis. In some embodiments, a ballast gas may be present in the epoxidation feed gas in a concentration of from 20 mole-% to 80 mole-%, relative to the total epoxidation feed gas, or from 30 mole-% to 70 mole-%, on the same basis.

Optionally, the epoxidation feed gas may further comprise a reaction modifier. If desired, a reaction modifier may be added to the epoxidation feed gas to increase the selectivity of the epoxidation catalyst. Examples of suitable reaction modifiers may include, but are not limited to, organic chlorides (e.g., $C_1$ to $C_3$ chloro hydrocarbons). Specific examples of suitable organic chlorides include, but are not limited to, methyl chloride, ethyl chloride, ethylene dichloride, vinyl chloride, and a combination thereof.

A reaction modifier may optionally be present in the epoxidation feed gas in a concentration of 0.1 parts per million by volume (ppmv) or greater, relative to the total epoxidation feed gas, or 0.3 ppmv or greater, or 0.5 ppmv or greater, on the same basis. Similarly, a reaction modifier is generally present in the epoxidation feed gas in a concentration of at most 25 ppmv, relative to the total epoxidation feed gas, or at most 22 ppmv, or at most 20 ppmv, on the same basis. In some embodiments, a reaction modifier may be present in the epoxidation feed gas in a concentration of from 0.1 to 25 ppmv, relative to the total epoxidation feed gas, or from 0.3 to 20 ppmv, on the same basis. Typically, as the epoxidation feed gas composition changes and/or as one or more of the operating conditions change, the concentration of reaction modifier in the epoxidation feed gas may also be adjusted so as to maintain the optimum concentration. For additional disclosure regarding reaction modifiers and optimum concentrations thereof, reference may be made to, for example U.S. Pat. Nos. 7,193,094 and 8,546,592, which are incorporated herein by reference.

Optionally, the epoxidation feed gas may be substantially free, and preferably completely free, of a nitrogen-containing reaction modifier. That is to say, the epoxidation feed gas may comprise less than 100 ppm of a nitrogen-containing reaction modifier, preferably less than 10 ppm, more preferably less than 1 ppm, and most preferably 0 ppm of a nitrogen-containing reaction modifier. As used herein, the term "nitrogen-containing reaction modifier" refers to a gaseous compound or volatile liquid that is present as, or capable of forming, nitrogen oxides in oxidizing conditions. Examples of nitrogen-containing reaction modifiers include, but are not limited to, NO, $NO_2$, $N_2O_3$, $N_2O_4$, $N_2O_5$ or any substance capable of forming one of the aforementioned gases under epoxidation conditions (e.g., hydrazine, hydroxylamine, ammonia, organic nitro compounds (such as nitromethane, nitroethane, nitrobenzene, etc.), amines, amides, organic nitrites (such as methyl nitrite), nitriles (such as acetonitrile)), and a combination thereof.

Processes of the present disclosure may further comprise contacting at least a portion of the epoxidation reaction product comprising ethylene oxide with lean absorbent in the presence of an iodide-containing carboxylation catalyst in an ethylene oxide absorber to yield a fat absorbent stream comprising ethylene carbonate and/or ethylene glycol and a recycle gas stream comprising a vinyl iodide impurity. In the ethylene oxide absorber, the epoxidation reaction product is brought into intimate contact with lean absorbent in the presence of an iodide-containing carboxylation catalyst, and optionally a hydrolysis catalyst. Typically, the lean absorbent comprises at least 20 wt % water, and preferably comprises from 20 wt % to 80 wt % water. Preferably, the lean absorbent also comprises ethylene carbonate and/or ethylene glycol.

Suitably, an ethylene oxide absorber comprises an inlet that is in fluid communication with an outlet of an epoxidation reactor, an inlet through which lean absorbent is supplied, and an outlet that is in fluid communication with the recycle gas loop. An example of a suitable ethylene oxide absorber includes a column comprising a plurality of vertically stacked trays, which provide a surface area for the lean absorbent and the epoxidation reaction product to come into contact. Preferably, the column comprises at least 20 trays, more preferably at least 30 trays. Preferably the column comprises less than 100 trays, more preferably less than 70 trays, most preferably less than 50 trays. Suitably, the ethylene oxide absorber may be the sort of reactive absorber described in EP 2178815 or in co-pending application EP 14186273.0.

The temperature in the ethylene oxide absorber is preferably from 50° C. to 160° C., preferably from 80° C. to 150° C., more preferably from 80° C. to 120° C. This is higher than the temperature in a conventional process and is required to promote the carboxylation and hydrolysis reactions. Temperature higher than 160° C. is not preferred as this may reduce the selectivity of the ethylene oxide conversion to ethylene glycol. Both the epoxidation reaction product and the lean absorbent are preferably supplied to the ethylene oxide absorber at temperatures in the range from 50° C. to 160° C.

The pressure in the ethylene oxide absorber is from 1 to 4M Pa, preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

The epoxidation reaction product stream supplied to the ethylene oxide absorber comprises carbon dioxide. However, it is possible that the epoxidation reaction product stream may contain insufficient carbon dioxide to achieve desired levels of carboxylation in the ethylene oxide absorber. Optionally, an additional source of carbon dioxide may be supplied to the ethylene oxide absorber, e.g. recycle carbon dioxide from a finishing reactor, carbon dioxide from a carbon dioxide recovery unit or, at start-up, carbon dioxide from an external source.

In the ethylene oxide absorber, the epoxidation reaction product is contacted with lean absorbent in the presence of an iodide-containing carboxylation catalyst and optionally a hydrolysis catalyst. Preferably, the epoxidation reaction product is contacted with lean absorbent in the presence of both an iodide-containing carboxylation catalyst and a hydrolysis catalyst. The carboxylation and hydrolysis catalysts may be homogeneous and/or heterogeneous. In one embodiment, the epoxidation reaction product is contacted with lean absorbent in the presence of both an iodide-containing carboxylation catalyst and a hydrolysis catalyst, and the lean absorbent comprises the catalysts.

Iodide-containing carboxylation catalysts suitable for use herein may be heterogeneous or homogeneous catalysts. Examples of suitable homogenous iodide-containing carboxylation catalysts include, but are not necessarily limited to, alkali metal iodides, such as potassium iodide, and organic phosphonium iodides or ammonium iodide salts such as tributylmethylphosphonium iodide, tetrabutylphosphonium iodide, triphenylmethylphosphonium iodide, and tributylmethylammonium iodide, and combinations thereof. Examples of suitable heterogeneous iodide-containing carboxylation catalysts include, but are not necessarily limited to, quaternary ammonium and quaternary phosphonium iodides immobilized on silica, quaternary ammonium and quaternary phosphonium iodides bound to insoluble polystyrene beads, and metal salts such as zinc salts immobilised on solid supports containing quaternary ammonium or quaternary phosphonium groups, such as ion exchange resins containing quaternary ammonium or quaternary phosphonium groups, and combinations thereof. Preferably the iodide-containing carboxylation catalyst is a homogeneous catalyst, most preferably an organic phosphonium iodide or alkali metal iodide.

Similarly, hydrolysis catalysts suitable for use herein may be heterogeneous or homogeneous catalysts. Examples of suitable homogenous hydrolysis catalysts include, but are not necessarily limited to, basic alkali metal salts, such as potassium carbonate, potassium hydroxide and potassium bicarbonate, and alkali metal metalates, such as potassium molybdate, and combinations thereof. Examples of suitable heterogenous hydrolysis catalysts include, but are not necessarily limited to, metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups, and combinations thereof.

A fat absorbent stream comprising ethylene carbonate and/or ethylene glycol is withdrawn from the ethylene oxide absorber via an outlet, preferably by withdrawing liquid from an outlet at the bottom of the ethylene oxide absorber. Preferably, at least 50% of the ethylene oxide entering the ethylene oxide absorber is converted in the ethylene oxide absorber. Preferably, at least 60%, more preferably at least 70%, even more preferably at least 80%, most preferably at least 90% of the ethylene oxide entering the ethylene oxide absorber is converted in the ethylene oxide absorber. The ethylene oxide may undergo carboxylation, providing ethylene carbonate. The ethylene oxide may undergo hydrolysis, providing ethylene glycol. Additionally, the ethylene carbonate that is produced from the ethylene oxide may undergo hydrolysis, providing ethylene glycol.

Optionally, a portion or all of the fat absorbent stream may be supplied to one or more finishing reactors (e.g., to provide further conversion of any ethylene oxide and/or ethylene carbonate that was not converted in the ethylene oxide absorber). Suitable finishing reactors may include a carboxylation reactor, a hydrolysis reactor, a carboxylation and hydrolysis reactor, and a combination thereof. Supply to one or more finishing reactors is preferred if a significant quantity (e.g. at least 1%) of ethylene oxide or ethylene carbonate is not converted to ethylene glycol in the ethylene oxide absorber.

Having generally described the invention, a further understanding may be obtained by reference to the following examples, which are provided for purposes of illustration and are not intended to be limiting unless otherwise specified.

EXAMPLE 1

An investigation of potential guard bed materials was undertaken with the understanding that effective guard bed materials would preferably exhibit a vinyl iodide removal efficiency such that the concentration of vinyl iodide in a recycle gas stream was reduced to ~1 ppbv or even sub-ppb-levels of vinyl iodide, while operating at conditions that are consistent with the process of the present invention. Suitable guard bed materials would also need to operate efficiently even at very high space velocities, as a high guard bed space velocity equates to a relatively small (and affordable) guard bed size relative to the catalyst bed size, and display thermal stability and complete inertness toward the feedstock components themselves.

Preparation of the Guard Bed Materials:

A variety of formulations were tested for guard bed effectiveness. These formulations are described in Table 1 with the method of preparation provided below.

Method 1 —Material was used "as-delivered" from vendor.

Method 2 —The indicated salt was dissolved in deionized water. Support material was vacuum-impregnated by immersing the support material in the salt/water solution while under vacuum, followed by breaking of the vacuum. The resulting impregnated support material was centrifuged at modest speed to remove excess liquid, followed by drying at 105° C. in flowing air.

Method 3 —Same as Method 2, with nitrates salts serving as sources of silver and potassium.

Method 4 —Guard bed material was prepared by a co-precipitation method wherein a solution of metal nitrates was prepared by dissolving metal components of aluminum, copper and zinc (in that order) in dilute nitric acid; a soda solution was prepared and transferred to a precipitation vessel and heated to 80° C.; the mixed nitrate solution was then added to the soda solution over approximately 2 hours while stirring while maintaining the temperature at approximately 80° C. The precipitation was stopped once a pH of 8.0 (+0.2) was achieved. The stirring of the slurry was continued for 30 minutes at 80° C. and the pH measured again. The precipitate was then filtered, washed, dried at a temperature in the range of from 120-150° C. and then calcined at a temperature of 400-500° C. The precipitate was then formed into 5×5 mm tablets, which were reduced using diluted hydrogen (0.1 to 10% volume H2 in N2) at 190 to 250° C. and the reduced tablets were then stabilized using dilute oxygen (0.1 to 10% volume O2 in N2) at a maximum temperature of 80° C.

Method 5 —Palladium and/or gold and/or bismuth formulations were prepared by dissolving sodium palladium chloride and/or chloroauric acid and/or bismuth nitrate in water; impregnating commercially available 5.4 mm diameter spherical silica (KA-160, manufactured and marketed by Sud Chemie); immersing the impregnated support material in aqueous sodium silicate solution; adding the reductant hydrazine hydrate to the solution; decanting excess liquid; washing with deionized water; drying in hot flowing air; impregnation with aqueous potassium acetate solution; decanting excess liquid; drying in hot flowing air.

Method 6—Same as Method 5 except the sodium silicate step was not included in the preparation.

Method 7—Same as Method 5 except the sodium silicate step and the hydrazine hydrate reduction step were not included in the preparation.

Method 8—Same as Method 5 except the hydrazine hydrate reduction step was not included in the preparation.

Method 9—Same as Method 5 except the potassium acetate steps were not included in the preparation.

Method 10—Same as Method 5 except a final water-washing step was added to the end of Method 5 to significantly reduce the potassium level of the material.

Testing of the Guard Bed Materials 2.00 g of candidate guard bed material was loaded into a ¼" internal diameter U-shaped stainless steel microreactor tube, and secured with plugs of glass wool affixed with steel screens at the inlet and the outlet of the bed. A feed stream comprising 25% v ethylene, 8% v oxygen, 1.1% v carbon dioxide, 2 ppm ethyl chloride, 1000 ppmv ethylene oxide, 1000 ppmv water, vinyl iodide at levels of 50-150 ppbv, balance methane, was directed through the guard bed at a flowrate of 800 mL/min, as the guard bed was maintained at a pressure of approximately 20.0 barg and a temperature of either 85° C. or 120° C., as indicated in Table 1. The vinyl iodide content of inlet and outlet streams was measured using a gas chromatograph equipped with an FID detector.

TABLE 1

| Candidate LR# | Candidate Guard Bed Material Description | Prep Method | Temp (° C.) | VI Fed (ppbv) | VI Exit (ppbv) | % VI Captured |
|---|---|---|---|---|---|---|
| Au- and Pd-Free Formulations | | | | | | |
| 25035-147-1 | Potassium Carbonate on alumina carrier | 2 | 85 | 92 | 121 | −32% |
| 27607-007-5 | Markes Carbograph Tenax | 1 | 85 | 87 | 99 | −14% |
| 27607-007-3 | Amberlyst 21 PVP resin | 1 | 120 | 83 | 85 | −2% |
| 27507-029-1 | 22 wt % Ag, 2.2 wt % K, alumina carrier | 3 | 120 | 65 | 65 | 0% |
| 27021-142-1 | Bismuth carbonate | 2 | 120 | 78 | 78 | 0% |
| 27607-007-2 | Reillex 425 PVP resin | 2 | 120 | 87 | 87 | 0% |
| 27308-098-1 | Cu/Zn on alumina carrier | 4 | 120 | 78 | 86 | 10 |
| 27215-028-2 | C-8-6-01 Activated Carbon | 1 | 85 | 111 | 110 | 1% |
| 27308-126-2 | 13X Molecular Sieves | 1 | 120 | 81 | 78 | 4% |
| 27507-067-1 | Cesium Carbonate on alumina carrier | 2 | 120 | 105 | 99 | 6% |
| 27021-143-2 | Bismuth nitrate/X-CY | 2 | 120 | 94 | 85 | 10% |
| 27607-007-4 | MgOZRO$_2$(from Noah tech) | 1 | 85 | 94 | 85 | 10% |

TABLE 1-continued

| Candidate LR# | Candidate Guard Bed Material Description | Prep Method | Temp (° C.) | VI Fed (ppbv) | VI Exit (ppbv) | % VI Captured |
|---|---|---|---|---|---|---|
| 27215-028-3 | PE 12x30 Activated Carbon | 1 | 85 | 87 | 78 | 10% |
| 27286-014-1 | CRI HS-PLUS catalyst | 1 | 120 | 66 | 58 | 12% |
| 27308-126-1 | LZY-52, a sodium Y Zeolite | 1 | 120 | 96 | 80 | 17% |
| 27215-027-6 | Ag/13X Molecular Sieves | 1 | 120 | 111 | 78 | 30% |
| 27021-142-1a | Bismuth Oxide | 1 | 120 | 163 | 110 | 33% |
| 27215-027-7 | Ag/LZY-52, a sodium Y Zeolite | 1 | 120 | 129 | 82 | 36% |
| 27507-081-1 | 5.0 wt % Ag, 2.2 wt % K, alumina carrier | 3 | 120 | 85 | 44 | 48% |
| Au and/or Pd-Containing Formulations | | | | | | |
| 27021-147-1 | 1.5 wt % Pd, 5 wt % Bi, alumina carrier | 5 | 120 | 81 | 63 | 22% |
| 26850-149-1 | 1.6 wt % Pd, K, silica carrier | 6 | 85 | 66 | 37 | 44% |
| 26850-151-2 | 0.8 wt % Au, K, silica carrier | 7 | 85 | 75 | 41 | 45% |
| 26850-149-2 | 1.6 wt % Pd, K, silica carrier | 7 | 85 | 72 | 27 | 63% |
| 26396-013-1 | 0.28 wt % Au, 0.53 wt % Pd, K silica carrier | 7 | 85 | 78 | 26 | 67% |
| 26850-148-1 | 1.6 wt % Pd, K silica carrier | 5 | 85 | 86 | 23 | 73% |
| 26850-148-2 | 1.6 wt % Pd, K, silica carrier | 8 | 85 | 90 | 20 | 78% |
| 26277-052-1 | 0.8 wt % Au, 1.6 wt % Pd, Bi silica carrier | 9 | 85 | 88 | 4 | 95% |
| 26850-146-2 | 0.8 wt % Au, 1.6 wt % Pd, K silica carrier | 8 | 85 | 83 | 1 | 99% |
| 27021-145-1 | 0.8 wt % Au, 1.6 wt % Pd, silica carrier | 10 | 85 | 88 | 0 | 100% |
| 27021-148-1 | KataLeuna KL7900 (0.8 wt % Au, 1.6 wt % Pd, K silica carrier) | 1 | 85 | 127 | 0 | 100% |
| 26850-147-2 | 0.8 wt % Au, 1.6 wt % Pd, K, silica carrier | 8 | 85 | 80 | 0 | 100% |

The results demonstrate that a guard bed material according to the invention is effective at reducing the amount of a vinyl iodide impurity in a recycle gas stream.

That which is claimed is:

1. A process comprising:
   contacting at least a portion of a recycle gas stream comprising a vinyl iodide impurity with a guard bed material to yield a treated recycle gas stream, wherein the guard bed material comprises a support material, palladium and gold; and
   contacting an epoxidation feed gas comprising ethylene, oxygen and at least a portion of the treated recycle gas stream with an epoxidation catalyst to yield an epoxidation reaction product comprising ethylene oxide.

2. The process of claim 1, further comprising:
   contacting at least a portion of the epoxidation reaction product comprising ethylene oxide with a lean absorbent in the presence of an iodide-containing carboxylation catalyst to yield a fat absorbent stream comprising ethylene carbonate and/or ethylene glycol and the recycle gas stream comprising the vinyl iodide impurity.

3. The process of claim 1, wherein palladium is present in the guard bed material in an amount of from 0.1% to 3% by weight.

4. The process of claim 1, wherein palladium is present in the guard bed material in an amount of from 0.8% to 2.2% by weight.

5. The process of claim 1, wherein gold is present in the guard bed material in an amount of from 0.1% to 3% by weight.

6. The process of any one of claim 1, wherein gold is present in the guard bed material in an amount of from 0.5% to 1.5% by weight.

7. The process of claim 1, wherein the support material comprises silica.

8. The process of claim 1, wherein the treated recycle gas stream comprises no more than 20 ppbv of vinyl iodide.

9. The process of claim 1, wherein the treated recycle gas stream comprises no more than 1 ppbv of vinyl iodide.

10. The process of any claim 1, wherein the treated recycle gas stream is supplied to a carbon dioxide absorber before being contacted with the epoxidation catalyst.

11. A reaction system for the production of ethylene carbonate and/or ethylene glycol comprising:
    a recycle gas loop fluidly connected to a source of ethylene and oxygen;
    an epoxidation reactor comprising an epoxidation catalyst, an inlet, and an outlet, wherein the inlet of the epoxidation reactor is fluidly connected to the recycle gas loop;
    an ethylene oxide absorber comprising an iodide-containing carboxylation catalyst, an inlet, and an outlet, wherein the outlet of the epoxidation reactor is fluidly connected to the inlet of the ethylene oxide absorber, the outlet of the ethylene oxide absorber is fluidly connected to the recycle gas loop, and the ethylene oxide absorber is configured to produce a recycle gas stream comprising a vinyl iodide impurity and a fat absorbent stream comprising ethylene carbonate and/or ethylene glycol; and
    a guard bed system comprising an inlet, an outlet, and one or more guard bed vessels comprising a guard bed material, wherein the guard bed material comprises a support material, palladium and gold, wherein the inlet and the outlet of the guard bed system is fluidly connected to the recycle gas loop, and the guard bed material is configured to remove at least a portion of the vinyl iodide impurity from at least a portion of the recycle gas stream.

12. The reaction system of claim 11, further comprising a carbon dioxide absorber fluidly connected to the recycle gas loop.

13. The reaction system of claim 11, wherein the guard bed system comprises two or more guard bed vessels.

14. The reaction system of claim 11, wherein palladium is present in the guard bed material in an amount of from 0.1% to 3% by weight.

15. The reaction system of claim 11, wherein gold is present in the guard bed material in an amount of from 0.1% to 3% by weight.

* * * * *